United States Patent [19]
Wittek

[11] Patent Number: 5,963,302
[45] Date of Patent: *Oct. 5, 1999

[54] PROCESS AND DEVICE FOR DIFFUSING PERFUMES THAT ACCURATELY CORRESPOND TO EVENTS OR SCENES DURING CINEMATOGRAPHIC REPRESENTATIONS AND THE LIKE

[76] Inventor: Götz-Ulrich Wittek, 500 Chesham House, 150 Regents Street, London W1R 5FA, United Kingdom

[*] Notice: This patent is subject to a terminal disclaimer.

[21] Appl. No.: 09/137,416

[22] Filed: Aug. 20, 1998

Related U.S. Application Data

[62] Division of application No. 08/931,456, Sep. 17, 1997, Pat. No. 5,832,320.

[30] Foreign Application Priority Data

Oct. 30, 1991 [DE] Germany .............................. 41 35 796

[51] Int. Cl.⁶ .................................................. G03B 19/18
[52] U.S. Cl. ................................ 352/38; 352/57; 352/85; 396/106; 40/106.22
[58] Field of Search .................................. 352/38, 57, 85; 396/106; 40/106.22

[56] References Cited

U.S. PATENT DOCUMENTS

| | | | |
|---|---|---|---|
| 2,562,960 | 8/1951 | Stern | 352/85 |
| 2,813,452 | 11/1957 | Laube | 352/85 |
| 3,795,438 | 3/1974 | Westenholz et al. | 352/38 |
| 4,629,604 | 12/1986 | Spector | 352/85 |
| 5,610,674 | 3/1997 | Martin | 352/85 |
| 5,760,873 | 6/1998 | Wittek | 352/85 |
| 5,832,320 | 11/1998 | Wittek | 352/85 |

OTHER PUBLICATIONS

Handbook of Chemistry and Physics, 13th edition, 1948, p. 1683.

Primary Examiner—Russell Adams
Attorney, Agent, or Firm—Burns, Doane, Swecker & Mathis, L.L.P.

[57] ABSTRACT

The invention relates to a process for intensifying sensorial perception of an audience in attendance of a visual and/or acoustic representation by introducing scents in synchronism with the visual and/or acoustic representations. The scents are supplied to or removed from the audience area either in groups or separately.

49 Claims, 8 Drawing Sheets

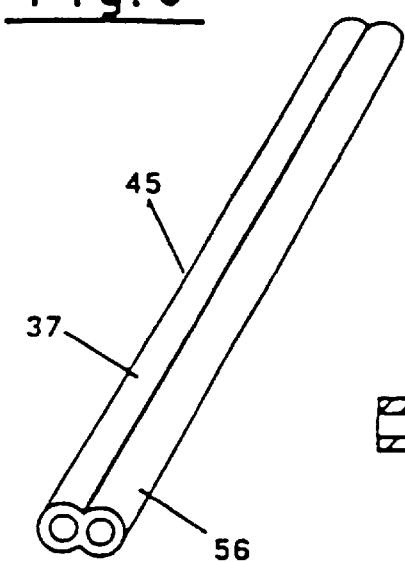
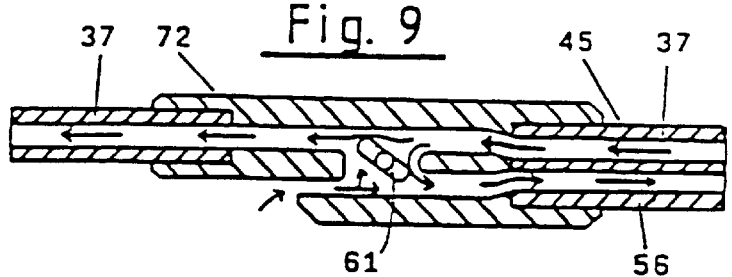
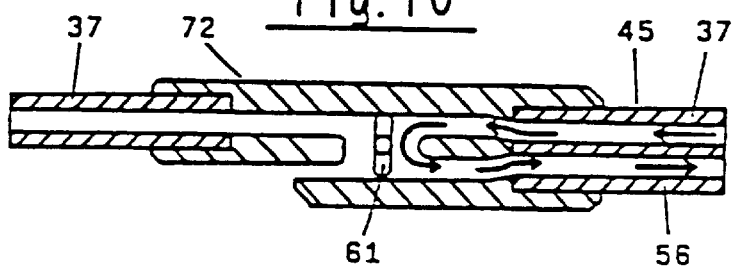
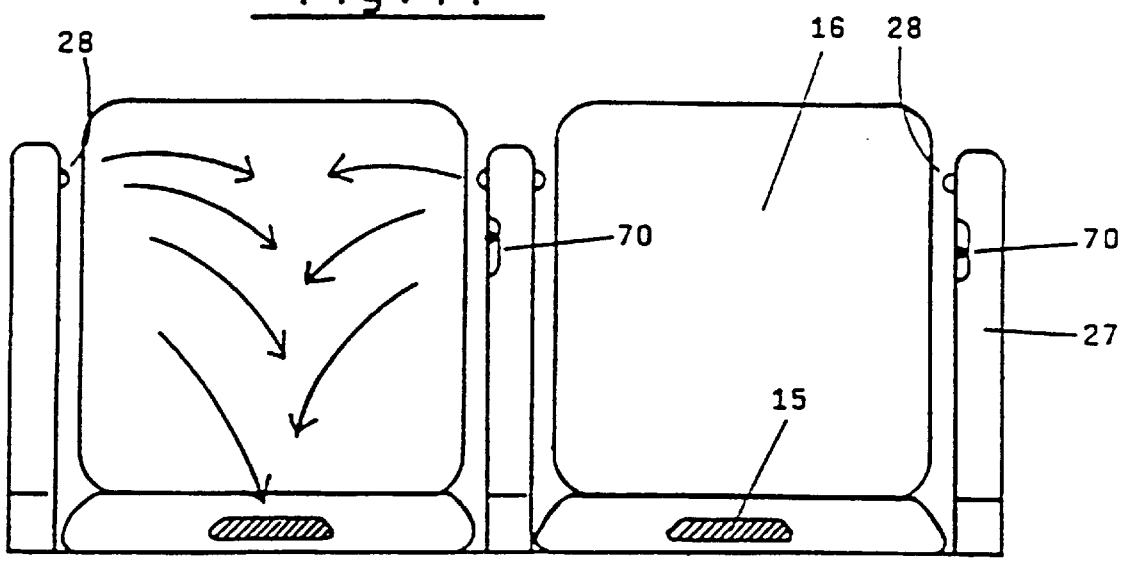

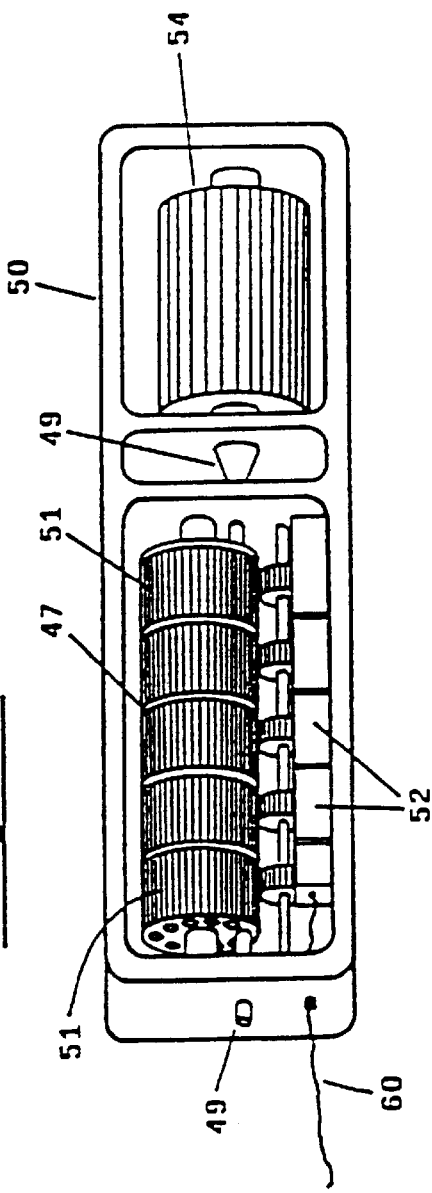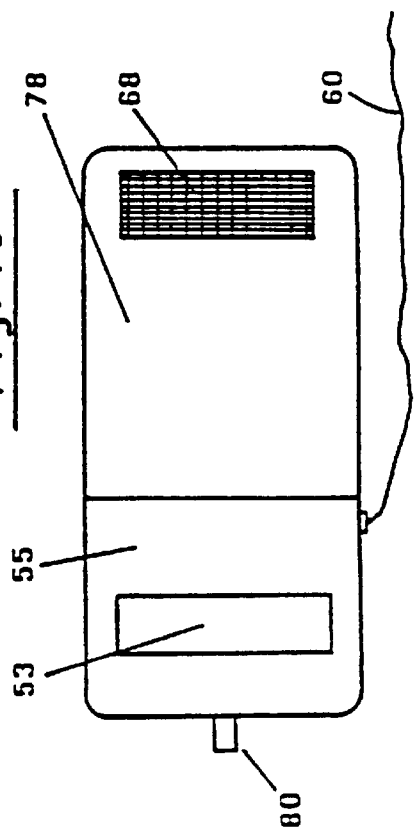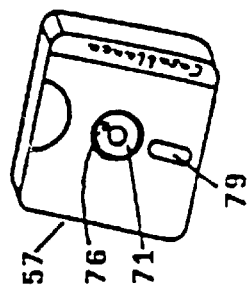

PROCESS AND DEVICE FOR DIFFUSING PERFUMES THAT ACCURATELY CORRESPOND TO EVENTS OR SCENES DURING CINEMATOGRAPHIC REPRESENTATIONS AND THE LIKE

This application is a divisional of application Ser. No. 08/931,456, filed Sep. 17, 1997 now U.S. Pat. No. 5,832,320.

The invention relates to a process for intensifying sensorial perception of visual and/or acoustic representations, in particular in cinemas, theaters, concert and conference halls, as well as during slide or video shows, television and radio broadcasts and the like, and to a device for carrying out such a process.

It is intended by way of the invention to include the audience to a larger extent in the performances and to extremely increase the fascination of the entertainment; at the same time, realisation of the system with respect to the device shall be as inexpensive as possible, specifically in the public sector.

The invention is based on the findings that the effect of visual and/or acoustic representations on the audience can be intensified by involving the sense of smell in the perception of events.

It has been known for a long time to gradually dispense scents in large rooms, halls and the like, as it has been done in Christian, Hindu and Buddhist churches for centuries, for example. This measure is intended to increase the inner involvement of the attendant worshippers. The perfumes or scents are usually supplied by one or two central fumigating lamps or the like; the scent of sandalwood, incense, etc. gradually spreads in the room and keeps on lingering there until fresh air is admitted upon conclusion of the ceremony.

Besides, attempts have been made in connection with the so-called "aroma therapy" to permeate offices or hospitals, e.g. Kajima Corp., Tokyo, and the Memorial Sloan Kettering Hospital, New York, respectively, with perfumes or scents via the existing air-conditioning systems. This method aims at producing certain stimulating or motivating effects, e.g. by introducing the scent of lemons in the morning to convey the feeling of freshness and activity. These are therapy-like measures which do not, and are not intended to, specifically intensify the effects of sensory perception of visual and/or acoustic presentations.

Another known method is the substantially manual, gradual distribution of a few scents or perfumes during theater and musical performances, such as the musical "HAIR" in 1969. It was a matter of supporting the effects of visual and/or acoustic presentations by releasing certain scents from a central position, similar to the above-described measure conducted in churches, which gradually spread in the auditorium in an uncontrolled manner. The scents were dispensed to accompany certain scenes but often reached the audience as a whole with a delay and then kept on lingering in the auditorium without being related to the subsequent scenes.

In 1981, a trial was conducted, in which tickets for the movie "Polyester" (directed by John Waters) were sold together with so-called "rubbing cards" comprising four numbered odors that could be released by rubbing the card. During the showing of the film, a number appeared on a certain place on the screen which corresponded to a number on the rubbing card; the spectator then had to rub the card in the area marked by said number, which led to the release of a specific (here: unpleasant) odor. In "Lexikon des internationalen Films", Vol. 6, p. 2973, Reinbeck/Hamburg, 1987, this odor is referred to as a " . . . gag offending the nose". This process had the disadvantage that every spectator had to release the odors manually himself/herself and was therefore clearly distracted from the visual and acoustic events, particularly as the scent card had to be held in front of the nose. Besides, the show was disturbed by understandable unrest in the auditorium, which was rather detrimental to the overall sensory perception of events.

It is an object of the present invention to provide a process and a device of the afore-mentioned kind by which the individual effects of various visual and/or acoustic events are intensified without requiring the cooperation of the audience and thus adversely affecting their concentration.

This object is solved by the process according to the invention as characterized by the features of patent claim 1 and by the device characterized by the features of patent claim 9. Further preferred embodiments of the invention which constitute advantageous developments of the process and the device can be taken from the respective subclaims.

The process and device according to the invention make it possible for the first time to provide the audience with different scents at exactly the right time and place in synchronism with associated movie scenes, sequences of music, etc., without requiring the cooperation of the audience. In this process, different scents are supplied in accordance with, and synchronous to, the respective events so that the events are rendered extremely realistic with respect to the suggestive and emotional effects thereof, which enables the audience to experience them in the original way.

This is favorably achieved by a variety of perfumes or scents from a scent reservoir whose intensities are preferably adjusted gradually to the individual events. Besides, the scents, whose intensities decrease or increase with time, can change—as in reality—in the manner of a fade-over and, in certain cases, can be mixed or superimposed. If, for instance, Jean Gabin drives through a meadow and then towards the sea, first the smell of meadows and grass will be perceived, followed by the known scent of sea water. In another example, John Malkovich kisses actress Debra Winger on the neck in a run-down hotel in Tangier in the movie "The Sheltering Sky", and the audience smells a bewildering blend of oriental perfume, the sweet scent of skin and the basic odor of mould in the hotel room.

The corresponding scents are supplied to the audience either in groups or separately; according to another embodiment of the invention, the scents are preferably evacuated in groups or separately during and/or after the associated events.

The device according to the invention advantageously comprises an arrangement for individually storing and releasing various scents and an associated arrangement for controlling the individual release and supply of scents in accordance with individual visual and/or acoustic events. The scent storing and releasing arrangement preferably has a number of different scent or perfume reservoirs which may be selectively made available by means of a scent supply selecting means. For this purpose, the stored perfumes are preferably provided in the form of releasable solids or liquids and can be emitted to a passing air flow by way of contact. Alternatively, the scents may be provided in the form of a gas or in the form of a fluid or aerosol and may be releasable under pressure. In both cases, it is guaranteed that scents are made available specifically as well as quickly and effectively.

According to a preferred embodiment of the invention, there is provided at least one scent switch box or scent disc or scent roll arrangement for storing the scents, said scent switch box being disposed either in the area of the controlling means or in the area of the audience. Preferably, the scent storing and releasing arrangement comprises a scent intensity controlling means in order to adjust the scents to the individual sensitivity of the people in the auditorium.

According to a preferred embodiment of the invention, the scent storing and releasing arrangement for introducing the respective scent into an air flow comprises a spiral-shaped conduit system which is slightly tapered in consideration of pressures and has inlet and outlet control elements and an associated bypass duct. Said perfume or scent storing and releasing arrangement for introducing the scent into an air flow may alternatively comprise at least two contact surfaces for associated parts of air flows. According to another alternative, the scent storing and releasing arrangement of the scent mixer can be designed for several basic scent components provided in scent mixing rolls that can be activated by single air flows.

The afore-mentioned alternatives or modifications of the perfume storing and diffusing arrangements can preferably be provided in cinemas, theaters, concert halls and the like as stationary units or, particularly in connection with scent discs or a scent mixer, as mobile units.

According to another embodiment of the invention, the scent storing and releasing device is designed such that the order of contacts with the scent mixing rolls is determined as a function of the scent intensity thereof so that the strongest scent component is contacted last. The scent mixer comprises a blower for generating the air flow. The scent reservoirs are protected against scent loss by openable sealing means and/or temperature-dependent release of scent; in the latter case, scents or perfumes are only released in certain temperature ranges.

The arrangement for controlling the individual release and supply of scents essential to the invention comprises a detecting means for individual event-related scent control signals, said detecting means being preferably designed to receive optical and/or electric scent control signals which contain encoded data on the type of scent and/or the compositions of scent and/or the scent reservoir switches and/or the frequency of use of the scent reservoir and the duration of scent supply. Furthermore, the scent control signals may preferably contain information on the scent intensity, the start and end of scent supply and the change of scents. Encoded film tracks or event-related signal transmitters are preferably used for scent control signals.

The arrangement for controlling the individual release and supply of scents comprises a source of compressed air which is connected to the arrangement for individually storing and releasing various scents and a subsequent scent distribution system. The compressed-air source advantageously consists of a compressed-air generator or compressor or a compressed-air storage means. The scent distribution system preferably comprises controllable scent outlets for groups of chairs and/or single chairs and is preferably equipped with main and intermediate distributors in order to guarantee the synchronous supply of scents.

According to another preferred embodiment of the invention, the scent distribution system includes a scent evacuation system for individual chairs and/or groups of chairs in order to intensify the individual effects of different scents in the order of their occurrence.

The scent distribution system is preferably provided with thin conduits whose lengths and diameters are adjusted to the distribution situation in the auditorium, the conduits being preferably designed as twin conduits with supply and return ducts for controlling the scent intensity individually at the seats.

According to another embodiment, the scents are supplied in the form of a scent/air mixture stream enriched with perfumes or scents, to which components of very low specific gravity have been added so that the emerging scent/air mixture is lighter than the ambient air.

In a particularly advantageous manner, a rotary whirling motion progressing in the direction of flow is imparted on the emerging scent/air mixture so that the mixture forms a directional hose-shaped stream over a predetermined distance after being discharged.

For this purpose, helically arranged elements, particularly small helically arranged ducts, are provided in the area of the outlet opening. Said helically arranged ducts provide a whirling stream of scent/air mixture in the area of the outlet opening within the outlet duct, said whirling stream leaving the duct in the form of a spiral.

At every seat, there are advantageously provided two outlet openings so that the two rotating streams of scent/air mixture perform rotary motions in opposite directions and sustain said rotary motions so as to additionally generate a tangential directional stream of scent/air mixture.

According to a particularly advantageous configuration, the scent outlets of the groups of seats and/or single seats are pivotably mounted to adjust the outlet opening of the scent/air mixture stream. For this purpose, ball-and-socket joints are preferably used.

Further details, advantages and features of the invention can be seen from the following description in which the invention is explained more closely with reference to the enclosed drawings.

In the following, 8 embodiments of the invention are described in more detail with reference to the enclosed drawings.

FIG. 8 is a view of a twin conduit (45), laid to all viewing chairs, of the embodiment of FIGS. 1 and 11, original size;

FIG. 9 is a longitudinal section through a viewing chair scent controlling means (72) of the embodiment of FIGS. 1, 8 and 11;

FIG. 10 is a longitudial section through the viewing chair scent controlling means (72) of FIG. 9 in the closed position;

FIG. 11 is a schematic view of a viewing chair (16) in an aroma cinema;

FIG. 15 is a schematic representation of a scent composer (50) of another embodiment;

FIG. 16 is a top plan view of a scent disc drive (55) of another embodiment of the invention;

FIG. 17 is a top plan view of a film scent disc (57) of the embodiment of FIG. 16.

Figure 1:
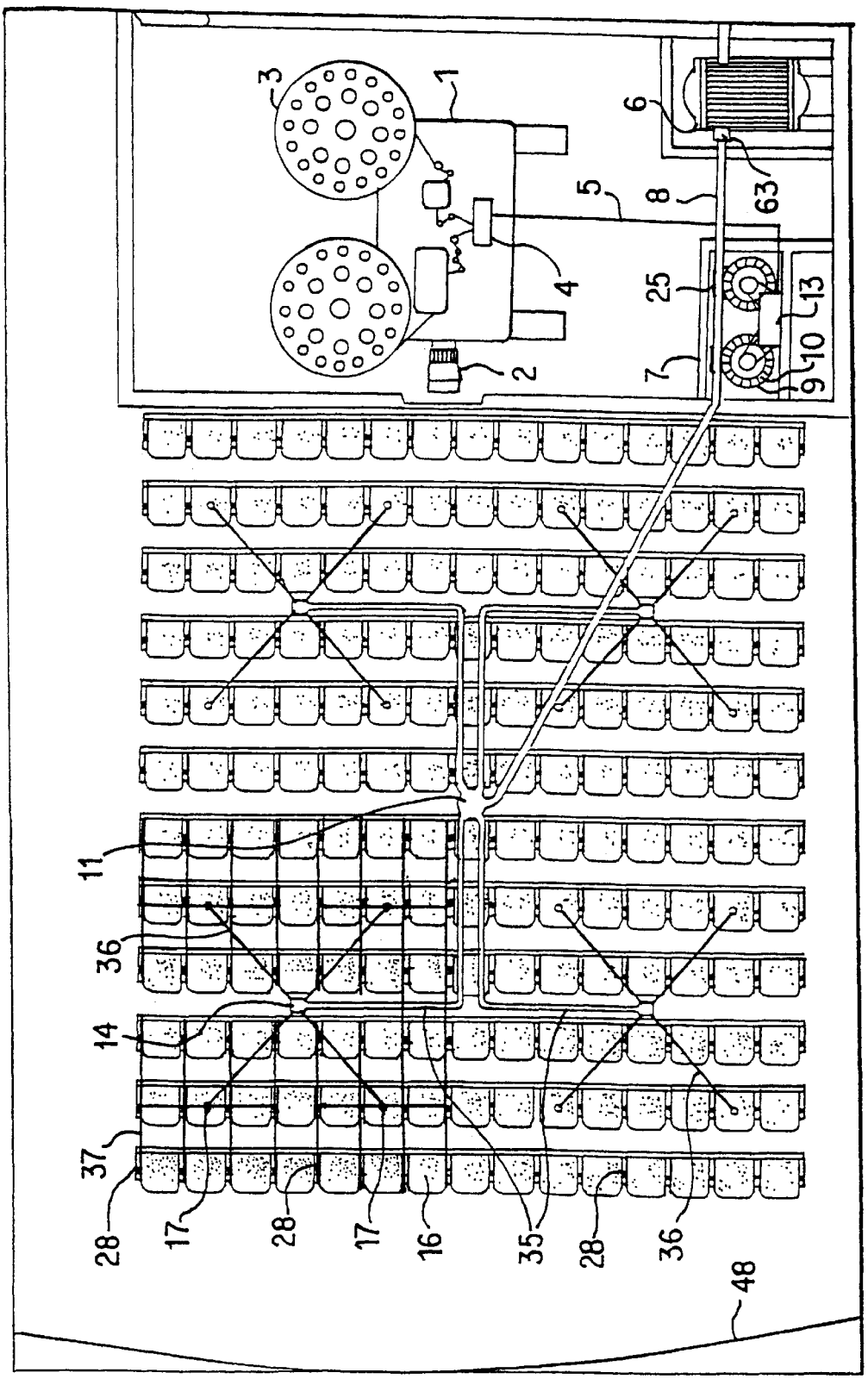
FIG. 1 is a schematic view of an embodiment of the aroma cinema.

The embodiment of the invention shown in FIGS. 1, 3, 4, 5, 6, 8, 9, 10 and 11 comprises a film projector 1 as depicted in FIG. 1, which includes, in addition to the usual equipment, such as projection lens 2, film rolls 3, etc., a pulse scanner 4 and a specific signal line 5.

The pulse scanner 4 is adapted to read specific control pulses 18–22 applied on the film 12 (FIG. 3) and to transform said pulses into electronic signals, for example.

Figure 5:
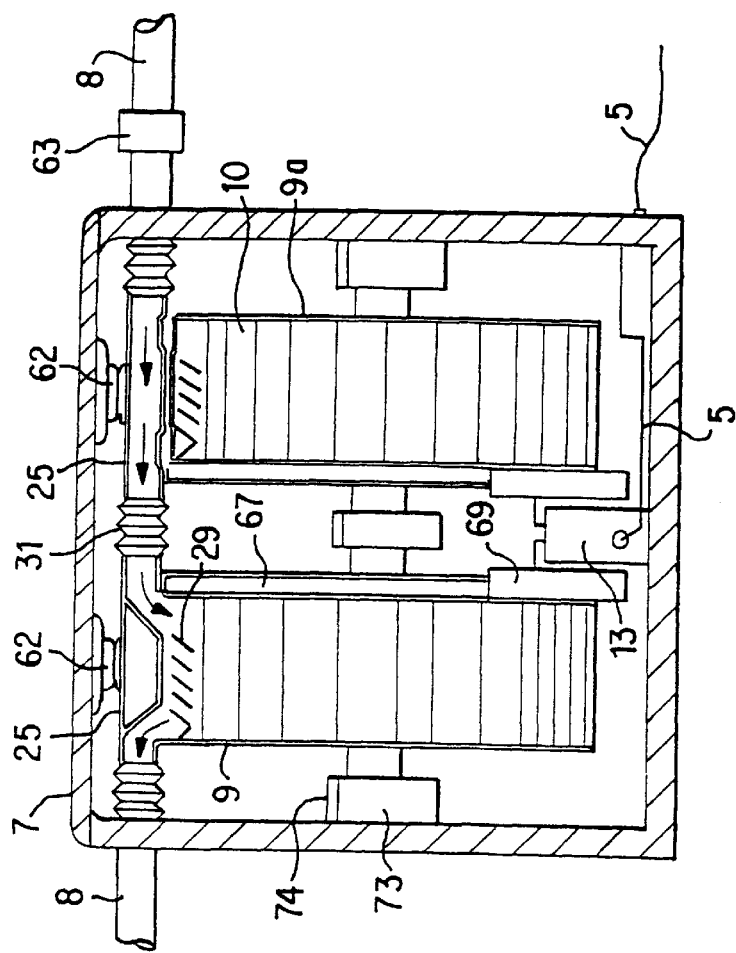
FIG. 5 is a lateral plan view with a partial section through the scent switch box (7) of FIG. 4 comprising a scent fade-over arrangement.
Figure 4:
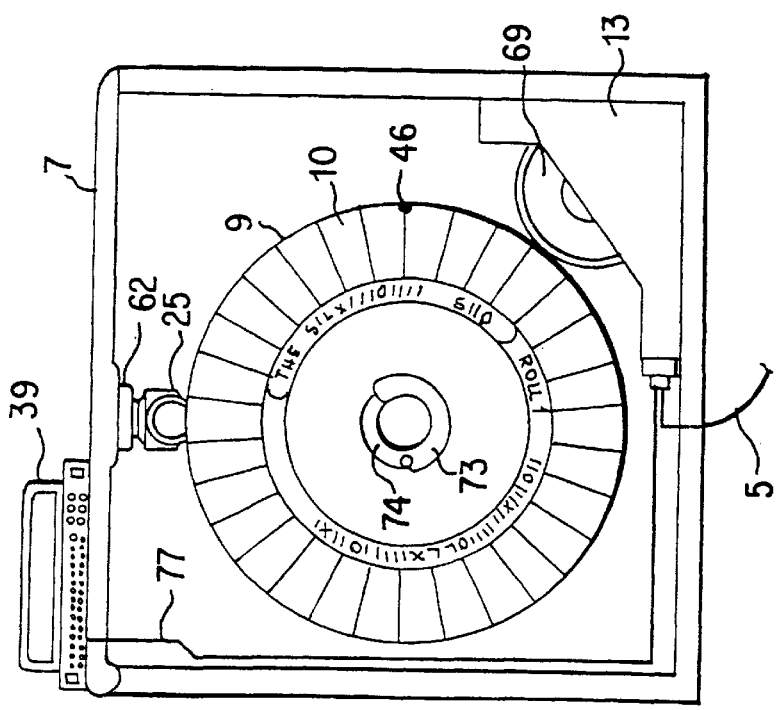
FIG. 4 is a top plan view with a partial section of a scent or perfume switch box (7) of the embodiment of FIG. 1.

The signal line 5 connects the pulse scanner 4 with a scent switch box 7 which contains several scent rolls 9 and 9a comprising a plurality of scent carriers 10 as well as a scent roll controlling means 13 (FIGS. 1, 4 and 5).

The scent switch box 7 is connected to a compressed-air conduit 8 which is supplied with compressed air by a compressed-air source, preferably an extremely low-noise electric compressor 6 or the like. The compressed-air conduit 8 extends from the scent switch box 7 to a main distributor box 11 where it is divided into several main conduits 35 leading to intermediate distributors 14.

In the intermediate distributors 14, the main conduits 35 are subdivided into smaller distribution conduits 36 leading to the final distributors 17 where the distribution conduits 36 are further subdivided into still smaller single conduits 37.

The single conduits 37 ultimately lead to the aroma armrests 27 of every single viewing chair 16 and open into a scent dispenser 28 (FIG. 11).

The purely schematic operation of the aroma cinema is as follows:

While during the showing of a motion picture, the usual optical and acoustic data are passed to the projection lens 2 and the audio heads of the film projector 1 via the film stock 12 and are projected on the screen 48 and fed to the loudspeakers, respectively, the film 12 preferably passes simultaneously through a pulse scanner 4 within the projector 1, said pulse scanner 4 scanning specific data with respect to a possible introduction of scents (FIG. 1).

The scent pulses 18–22 scanned (FIG. 3) can be stored in electronic, optical or some other form on the sound track, depending on the kind of film, on a compensating track or on appropriate special tracks or film components.

Instead of controlling the data relating to the introduction of scents and perhaps further additions to the movie performance via pulses 18–22, it is also possible to store the data by way of specific, electronically readable film bar-codes 30 (FIG. 3) which can be read from the running film stock 12 by a corresponding electronic bar-code film scanner (not shown) during the showing of the film.

Hence, the film bar-codes 30 are not optically stored like usual bar-codes but preferably are magnetic bar-codes in non-perceptible frequency ranges. They can therefore be additionally placed as meta information on an already pre-recorded sound track without the code signal becoming audible or the sound of the sound track being impaired in any way.

The afore-described scent pulses 18–22 can also be applied as meta information on already existing film stock in various ways.

It is thus possible to subsequently encode old film stock without major changes, if necessary, so that old projectors only have to be equipped with appropriate code or pulse scanning devices without requiring any other major technical modification.

Another alternative with respect to the pulse commands 18–22 is a control pilot signal 34 (FIG. 3) which does not give a control command in the form of "on" or "off" but whose control commands are only effective as long as the signal is emitted. As soon as the signal stops, the controlled function is stopped, too, which may be advantageous for some of the operations described in the following.

The stored pulse 18–22 (FIG. 3) is read by the pulse scanner 4 (FIG. 1) and transformed into an electronic signal, for example, and passed on to the scent roll controlling means 13 of a scent switch box 7 via the signal line 5 (FIGS. 1, 4 and 5).

The scent switch box 7 is connected to a compressed-air conduit 8 which is fed by a low-noise compressed-air source, e.g. a very low-noise electric compressor 6, which is arranged within the projectionist's cabin (FIG. 1).

In response to the incoming control signal, the scent roll controlling means 13 activates the associated scent on the scent roll 9. The scent roll 9 rotates a little so that the respective scent carrier 10 is positioned exactly in front of the scent connecting piece 25 (FIGS. 1, 4, 5 and 6).

Figure 3:
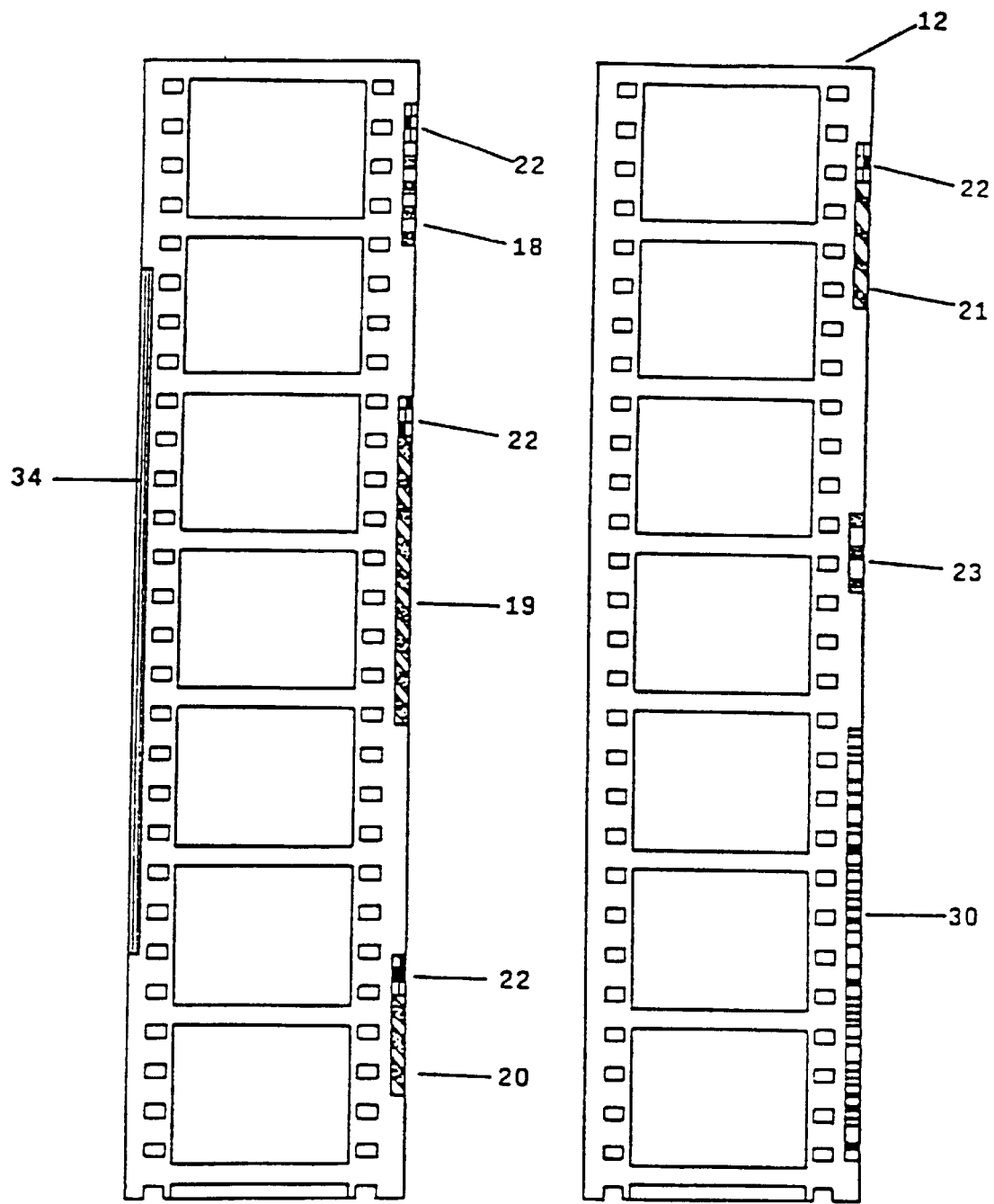
FIG. 3 is a schematic representation of film stock (12) of the embodiment of FIG. 1 with scent pulses.

The scent carrier 10 is specifically activated by the "precode" signal 18, while the signals 19–21 control other operations, as will be described in more detail in the following (FIG. 3).

As regards the present embodiment of the compressed-air conduit 8 (FIG. 5) and the branches thereof, the scent connecting piece 25 advantageously is pressed slightly against the scent roll 9 or the scent carrier 10 by a device, e.g. the contact mechanism 62, after the scent carrier 10 has been introduced.

The contact edges of the scent connecting piece 25 are preferably provided with sealing materials 24 (FIG. 6) so that a closed, sealed system is obtained.

During the pressing or contact operation of the contact mechanism 62, the minimum space between the scent roll 9 and the scent connecting piece 25 required for the rotational mobility of the scent roll 9 is bridged (FIGS. 4 and 5).

The space between the scent roll 9 and the scent connecting piece 25 preferably is about 1 mm.

The compressed-air conduit 8 is presumed to be sufficiently resilient in most cases. If the compressed-air conduit 8 is made of a very unflexible material or is very thick, however, the mobility of the compressed-air conduit 8 required for the pressing operation is guaranteed by inserting flexible pipe collars 31 before and after the scent connecting piece in this embodiment (FIG. 5).

Figure 6:
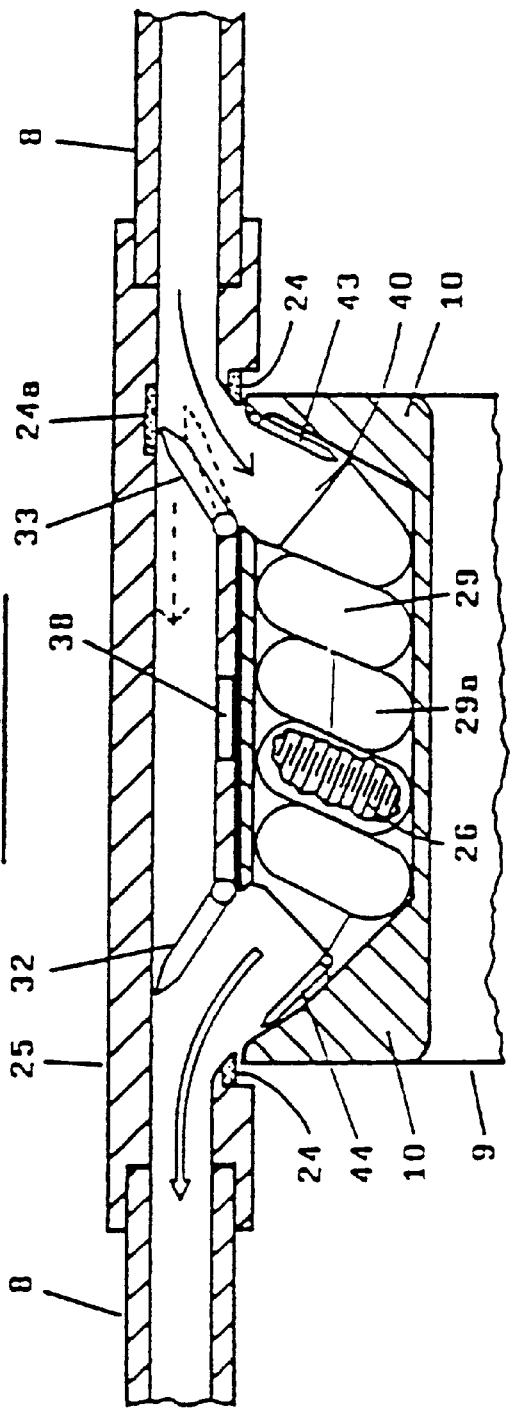
FIG. 6 is a longitudinal section through a scent connecting piece (25) and a scent carrier (10) of the embodiment of FIGS. 4, 5 and 1.

When the scent carrier 10 has been fastened in the scent connector 25, the scent intensity controlling means 33 is opened completely (or partially, cf. the scent intensity controlling means shown in dash lines), with the airflow controlling means 32 being opened to the same extent at the same time (FIG. 6).

The airflow from the compressed-air conduit 8 is conveyed to the inlet opening 40 of the scent carrier 10 (FIG. 6). (In case of a partial opening only - cf. air flow controlling means 33 indicated in dash lines, corresponding to 32 -, part of the air is guided past the scent carrier 10 after the scent intensity controlling means 33, 32 has opened, as will be described in more detail further below).

The scent carrier 10 may additionally be equipped with sealing flaps 43 and 44 or corresponding types of valves (FIG. 6) which are biased e.g. by a simple metal spring or the like in a sealing manner and simply yield to the force of the airflow, or which are opened electronically.

Alternatively, the sealing flaps 43, 44 may be opened mechanically by a projection (not shown) or the like when the scent carrier 10 is pressed against the scent connecting piece 25 (FIG. 6).

The sealing flaps 43, 44 can also prevent the perfumes or scents stored in the scent carriers 10 from volatilizing before they are actually used.

Besides, the formation in scent switch box 7 of an unpleasantly smelling hodgepodge of all the scents stored in the scent roll 9 can thus be prevented, which otherwise might get into the airflow when scents are introduced therein.

Whether the scent carrier 10 is provided with additional sealing flaps 43, 44 substantially depends on the kind of storage and the volatility of the scents; i.e. in inert storage systems, they are not required.

In the system according to another embodiment (FIG. 12), which is inert when the air is not in motion and which does not have any sealing flaps 43, 44, only a small amount of the airflow from the compressed-air conduit 8 is passed into the scent carrier 10. The scent connecting means 25 rather is designed such that a certain negative pressure is generated in the conduit region above the outlet opening 42, so that the air is sucked from the compressed-air conduit 8 instead of being forced thereinto.

Figure 12:
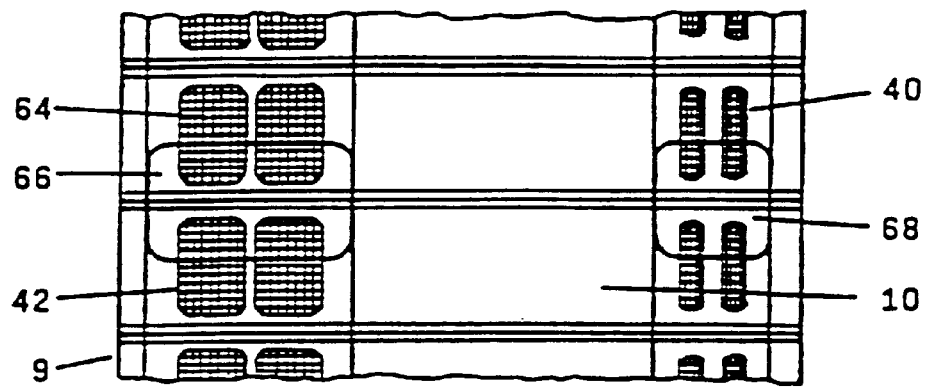
FIG. 12 is a top plan view from above of two scent carriers (10), with a schematic representation of a negative pressure scent connecting piece (25*a*) of another embodiment.

This system has the advantage that the sealing flaps 43, 44 may be dispensed with and the openings are only covered by a close-meshed so-called scent grid 64 (FIG. 12). Besides, the contact mechanism 62 and the sealing of the scent carrier 10 are not required in the embodiment of FIG. 12.

After the airflow has passed the inlet opening 40 or the sealing flap 43 of the scent carrier 10 in FIG. 6, it arrives at a preferably helical conduit system, the scent helix 29 (FIG. 6).

In the scent helix 29, there is preferably provided a very large number of scent lamellae 26 arranged in a fan-shaped manner (FIG. 6) which consist of solid and highly porous materials (e.g. silicone sponge or the like).

In the scent lamellae 26 arranged in fan-shaped manner, a large amount of scents or perfumes are stored, preferably in dry form, which are given off into the stream of supplied air as it passes through.

So as to obtain a uniform air resistance in the scent helix 29 between the scent lamellae and the airflow passing through, it may be useful to provide a duct diameter in the helix which is continuously tapered towards the end of the spiral so that the conduit is both spiral-shaped and slightly conical.

In this configuration, the most varying kinds of scent contacts and scent storage are possible. Likewise, the airflow can be passed through the scent carrier or the scent roll in several ways; e.g. the duct may be situated within the scent roll and extend through the scent carrier from the scent roll, etc.

By combining spiral-shaped conduits in the scent helix 29 (FIG. 6) with the fan-shaped arrangement of the scent lamellae 26 as well as the porous, foam-like surface of said scent storage systems, an extremely large surface of scent-bearing parts is obtained on the whole.

As a result, a considerable diffusion of scents is achieved even if only small amounts of air pass through.

Said thorough enrichment with scents is also important because the diameters of the scent-bearing conduits 37 leading to the spectators are extremely small, as will be described below.

As a result of the large surface of the scent-bearing parts in the scent helix 29 in conjunction with the dry storage of perfumes, the materials in the scent helix 29 can emit the scent many times so that a scent carrier 10 or a scent roll 9 can be used for a large number of motion picture shows.

When the scent rolls 9 of the scent switch box 7 are finally exhausted, they can be replaced by the projectionist.

The unit scent switch box 7 can also be designed such that it can be separated as a whole from the conduit system 8 and the scent roll controlling means 13 and replaced.

The preferred and least expensive way of recycling used scent rolls 9 is to simply immerse the used scent carriers 10 in liquid substances of corresponding perfumes in installations especially equipped for this purpose, whereupon the scent lamellae 26 of the scent helix 29 get soaked with the odorous substances which are retained therein in concentrated form after drying. To facilitate the storing of new scents and to cut short the drying operation, the scent carriers 10 and the scent helix 29 may be designed such that they can be unfolded in the middle.

The scent helix 29 is thus divided into upper and lower halves 29a (FIG. 6) and easily accessible from outside.

This design facilitates the manufacturing process and results in a considerable reduction of costs. If the new cinema system is used widely enough, it will be possible to provide various relatively inexpensive expendable systems of scent rolls 9, scent carriers 10, scent helix 29 or other scent-bearing systems.

The degree to which the air from the compressed-air conduit 8 is enriched with perfumes in the scent helix 29, and in particular the speed at which said enrichment takes place, depend largely on the position of the scent intensity controlling means 33 and the airflow controlling means 32.

It is possible, for instance, to introduce the desired perfume only weakly, i.e. the controlling means 32 and 33 only feed a little of the airflow into the scent helix 29, and the main airflow is further guided past the scent carrier 10 (FIG. 6, see the scent intensity controlling means 33 represented by dash lines).

Corresponding positions of the scent intensity controlling means 33 which opens only slightly (FIG. 6, represented by dash lines) and, likewise, of the airflow controlling means 32 are obtained in that the running film stock 12 first gives off only a partial pulse 20 (=slight emission-of scent) instead of a full pulse (=full emission of scent) to the pulse scanner 4 (FIGS. 1 and 3).

The pulse scanner 4 then supplies a corresponding "smaller" signal to the scent roll controlling means 13.

The scent roll controlling means is connected to a control system 38 which controls the controlling means 32, 33 and supplies it with the "small" control command for the scent intensity controlling means 32, 33, whereupon the latter are only opened to a correspondingly small degree.

In this manner, only a weak scent is emitted from the scent helix 29 or corresponding other scent-bearing systems (FIG. 6, representation in dash lines).

On account of these control steps, any number of nuances regarding the intensity of the respective perfume can be obtained depending on the intensity of the partial pulses 20/21.

Any further opening of the scent intensity controlling means 33 and the airflow controlling means 32 along with a corresponding change in scent intensity can be controlled by further partial pulses 20 or a full pulse 19, depending on the film events.

By way of this technique, certain scent events of the film which should only be perceivable very slowly according to the story of the film can be "faded in" just as slowly (e.g. a young couple walks out of town and gradually gets out in the open: at first the scent of grass and trees can hardly be perceived but gradually gets stronger).

Said fade-in technology can also be performed the other way round, of course, i.e. a scent can gradually be "faded out", as the completely open scent intensity controlling means 33 (as well as the airflow controlling means 32) close only gradually on account of "negative partial pulses" 21. (Example: A man walks from the harbour—accompanied by the typical harbor and sea smells—into town; on his way, the harbor smell disappears gradually.)

The third important way of continuously changing scents is "crossfading", which can be achieved by cooperation of the scent roll 9 and a second scent roll 9a disposed in the scent switch box 7 (FIG. 5). In the crossfading operation, a second scent is made perceivable for a short time while another scent is already lingering. (Example: People party in a room which smells slightly of wood and smoke; a lady walks through, accompanied by the smell of scent, which masks the previous smell for a short time.)

Crossfading of two different scents is achieved very easily; a scent stored in the second scent roll 9a is introduced into the compressed-air conduit 8 while another scent is already being fed in, e.g. from scent roll 9 (FIG. 5; however, the scent intensity controlling means 33, 32, which are only schematically represented, are open in scent roll 9a as well as in scent roll 9 for the crossfading step, see FIG. 6.)

If necessary, the scent from the first scent roll 9 can be weakened for a short time during the crossfading step by the scent from the second scent roll 9a and subsequently be increased again.

By employing the second scent roll 9a, it is possible to introduce two scents immediately one after the other, which is probably not feasible with a single scent roll.

In order to bring about a quick change of scents, if only a single scent roll 9 is used, the airflow will have to be interrupted first, the scent carrier 10 disconnected with the scent connecting piece 25, a new scent carrier selected and switched on, and finally air will have to be introduced again. If, moreover, the introduced scent takes some time to arrive at the spectator (see further below under "synchronization"), it is clear that a quick sequence of scents is extremely difficult to achieve when only a single scent roll 9 is available.

The perfumes or scents which are to succeed one another quickly according to the events of the film are therefore preferably stored alternatingly on the scent rolls 9 and 9a to ensure a fast change of scents.

Hence the director of the film can determine the speed of a scent change in accordance with the events of the film almost at will, as the alternating activation of the scent rolls 9 and 9a provides a means to effect quick scent changes.

For such a completely new medium in the art of cinematography, a novel way of cinematic expression will probably develop over time, as it happened after the introduction of sound film. It is difficult to foresee what demands will then be made on the new medium.

If it turns out during the employment of the new medium that an even faster change of scents is desired in certain cases to accompany film scenes, the scent switch box 7 could then also be equipped with a third scent roll (not shown).

On such a third scent roll, special scents required for screen advertising or for the promotion of new movies in the form of trailers could also be stored. As long as a third scent roll is not substantially required, the scents for advertising films and trailers, etc. are stored on one of the scent rolls 9 or 9a.

By using said techniques of fading-in, fading-out and crossfading as well as quick scent changes, there are hardly any movie situations conceivable which cannot be mastered in respect of the accompaniment with scents.

If several movies are shown in the same movie theater on a single day, the scent for the other movies is passed through another scent roll or another scent switch box 7. If, for instance, movie 1 is shown in the afternoon, movie 2 in the evening and movie 3 at night in the same theater, there are advantageously provided three scent switch boxes 7 in the projectionist's cabin (not shown).

In order to avoid having to connect another scent switch box 7 to the scent connecting piece 25 every time another movie is shown, the three scent switch boxes 7 which are arranged side by side are connected to three separate scent connecting pieces 25 which are all connected to the compressed-air conduit 8.

When the program changes, the projectionist simply switches the scent connecting piece 25 to the corresponding movie. In an improved version of the system, every movie is able to switch on the pertaining scent connecting piece via a corresponding scent connecting piece signal itself.

Figure 7:
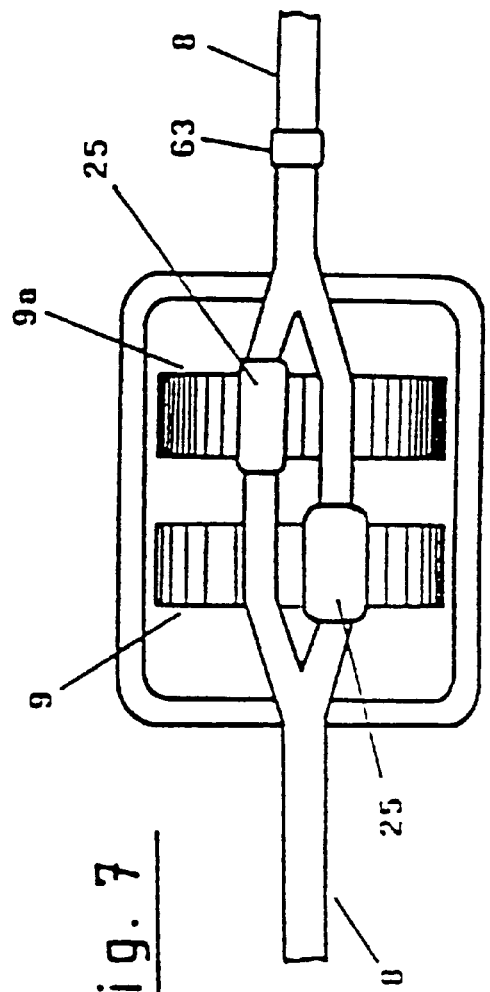
FIG. 7 is a top view from above of a separate scent fade-over arrangement of another embodiment.

The embodiment shown in FIG. 7 is particularly designed to avoid problems which might arise in the above-described technique of scent crossfading.

In said method of short-term crossfading of scents, the problem of socalled "aroma transfer" may arise when scents are frequently crossfaded within a single conduit 8 (FIG. 5).

A strong scent confined in the second scent roll 9a, which is introduced in the first scent roll 9 containing a weak scent for crossfading (see FIG. 5; the controlling means of both scent rolls being open, however) may have completely supplanted the first scent in the scent roll 9a after the movie has been shown several times.

(Example: In an old Italian villa having a slight inherent smell which has already been introduced to the audience, the leading actor shown in a long shot lights a match in semi-darkness: the inherent smell of the house is supplanted by the typical smell of sulphur for a short time.)—Possible result: After several showings of the movie, the scent carrier 10 of the first scent roll 9 comprising the inherent smell of the house which is used for several scenes in the movie has already adopted a strong sulphurous smell from the second "faded-in" scent carrier 10 of the scent roll 9.

In the next showing of the movie, the smell of matches which is to be faded in for a moment only will then already be perceivable when the first scent roll 9 comprising the smell of the house is openend, which would give the wrong impression to the audience that the whole house is burning. In order to avoid such a problem, it is advisable to divide the compressed-air conduit 8 of the embodiment of FIG. 7 in the area of the scent rolls 9 and 9a.

In this case, the scents or perfumes are introduced in separate conduits when crossfading from the two scent rolls 9 and 9a is desired, so that the actual crossfading effect only takes place after the scent rolls in the reunited compressed-air conduit 8 (FIG. 7).

In this manner, the transfer of scents from one scent roll 9a to the other scent roll 9 (FIG. 5) which may occur in the course of crossfading is reliably prevented (FIG. 7).

An analysis of about 50 renowned movies with respect to a change of scents has shown that most movies comprise only about 20 to 35 scenes which it makes sense to accompany with different scents.

However, there usually are about 5 to 10 main scene locations which appear several times and whose smells therefore recur (e.g. a certain room, an apartment, a certain car, a certain region, such as a forest, etc.).

On average, about half of the main scene locations would probably not be associated with scents of their own. The other half recurred about 2 to 12 times, about 7 times on average, which means that the corresponding smells would recur just as often.

For this reason, the whole scent equipment of a movie can be considerably simplified by not storing every scent on a separate scent carrier 10 in the scent roll 9 but by providing the frequently recurring scents of a main scene location on a single or on two scent carriers 10 which may be designed somewhat larger for this purpose.

In such a configuration, e.g. the four scents to be associated with main locations will be faded in from the same scent carrier 10 about 7 times on average, which means that about 24 scent carriers can be saved.

Accordingly, it can be seen from FIGS. 3a and 5 that several larger scent carriers are provided on one of the two scent rolls 9 or 9a. In this configuration, corresponding pulses which repeatedly activate the recurring scent carriers are applied onto the film stock.

The above-described gradual increase in the intensity of a supplied scent by adjusting the controlling means 32 and 33 accordingly permits another interesting application.

As already mentioned in the description of the scent carriers 10, the intensity of the scent release by the scent helix 29 diminishes after several showings of the movie. So as to prevent the last third of all showings that can be carried out with one scent roll before the scent roll is completely exhausted from being accompanied by inadequately weak scent pulses, the scent roll controlling means 13 which also controls the scent intensity controlling means 32, 33 via the control system 38 can be equipped with an electronic amplifying loop.

The amplifying loop counteracts the fading of the scent pulses by selecting, as from the last third of possible performances, continuously higher degrees of scent intensity than were originally activated via the controlling means 32 and 33.

In this case, the degree of opening of the scent intensity controlling means 33 (as well as the degree of closure of the airflow controlling means 32) is selected somewhat larger than originally in response to the same signal. In this manner, an ever weaker release of scents from the scent helix 29 is counteracted, and continuously compensated for, by an increasingly strong introduction of scents via the controlling means 32 and 33.

In this process, a full pulse 19, which already includes the full release of scents, can actually not be further intensified. So, in order that the intensity of a full pulse may be maintained, the scent carriers 10 are so adjusted that in standard operation, i.e. before the release of scents grows weaker, they already emit the full scent (according to full pulse 19) at an opening degree of 70% of the scent intensity controlling means 33, for example. The scent intensity controlling means 33 (corresponding to controlling means 32) can thus readjust the scent intensity up to an opening degree of 100% before the scent roll 9 finally has to be replaced.

The extent of readjustment of scents by the scent roll controlling system 13 can be controlled by a counter disposed therein, which activates the continuously increasing amplifying loop as from a certain number of movie shows. Said readjustment can even be made dependent on specific scent carriers, if the effects of certain scent carriers 10 abate more than others.

The pertinent information could be placed at the beginning of the film 12, just like all the other signals (FIG. 3), for example, and could be passed on via the pulse scanner 4 to the scent roll controlling means 13 which individually readjusts the scent intensity via the controlling system 38 and the controlling means 33/32. When a new scent roll 9 is installed, the counter is reset at "zero".

After the airflow has passed through the scent helix 29 and has been enriched with perfumes or scents according to the setting of controlling means 32 and 33 (referred to as "enriched" hereinafter), it passes the sealing flap 44 at the end of the scent helix 29 and is reintroduced into the compressed-air conduit 8 and conveyed further by the subsequent compressor-generated pressure.

The "enriched" air then passes through the compressed-air conduit 8 in the middle of the movie theater to the main distributor 11, where the compressed-air conduit is divided into several, e.g. four main conduits 35 (FIG. 1). From there, the enriched air is conveyed to several intermediate distributors 14 in distributing conduits 36, further to the final distributors 17 and finally via the single conduits 37 to the scent releasors 28 in the armrests 27 of the single viewing chairs 16, i.e. to the spectators (FIG. 1). The exact structural and chronological process will be described in more detail below.

So as to be able to keep track of the afore-mentioned control operations and the functions to be described in the following, it may be useful to render the operations visible. For this purpose, the scent switch box 7 can be equipped with a control terminal 39 comprising a screen and a keyboard (FIG. 4).

On the screen of such a terminal 39, all steps of the whole scent control operation are recorded. The current text as well as a designation of the scenes are displayed, and marks are inserted next to the text to indicate the position and the kind of relevant signals and control commands. The adjustment of the afore-described amplifying loop adapted to each scent carrier in the scent roll controlling means 13 can be displayed and monitored. If, for some unforeseeable reason, the scent roll controlling means 13 selects perfumes or scents that are either too strong or too weak and feeds them into the compressed-air conduit 8, this step can be readjusted via terminal 39.

For control purposes, a single scent conduit 37 may also be extended to the projectionist's cabin so that the projectionist can check himself the intensity of the released scent on request.

A further alternative of scent control which might even be more accurate than the afore-mentioned measures is the installation of a scent analyser (not shown) which is also connected to the control terminal 39 or directly to the scent roll controlling means 13.

Although the scent analyser, if it is not to be unreasonably expensive, cannot specify a certain scent itself, it is adapted to electronically analyse the airflow on the basis of the initial data of the full pulse to determine the amount (percentage) of scent introduced into the distribution network in response to a full pulse 19.

If the measured data deviate considerably from the preset data, the scent intensity can be corrected in response to corresponding readjustment signals from the scent analyser either via the scent roll controlling means 13 (which also controls scent intensity via the controlling means 33 and 32) or via the control terminal 39.

The course of individual functions involved in the release of scents during the showing of motion pictures has now been schematically described.

So as to be able to produce a perfect piece of motion picture art with the aid of the above-described technologies, however, the supply of perfumes or scents accompanying scenes of motion pictures shall also meet the following demands on its way from the projector to the spectator:

1.) Quick transfer of scent in conjunction with extreme reduction of air volume (speed and minimization);

2.) It must be possible to make the scent perceivable to the spectator simultaneously with the associated scene on the screen (synchronization of scenes);

3.) The scent must meet the requirement of 2.) not only for one spectator but for the whole audience in the entire movie theater at the same time (simultaneous perceptibility);

Ad 1.) Speed and minimization: The micro air system.

For carrying out the entire process of supplying scents in accordance with scenes of the movie, it is very important that the scent be conveyed quickly and precisely from the scent carrier 10 to the viewing chair 16 and the spectator.

For this purpose, it is essential that the amount of air required for conveying the scent from the scent carrier 10 to the viewing chair 16 be maintained as small as possible, as otherwise there would probably arise serious problems, such as unpleasant superposition of single perfumes or scents in the showroom of the movie theater, loud noise caused by large, displaced quantities of air, or air circulation which disturbs the audience, not to mention the required gigantic compressor.

So as to minimize the amount of air emerging at the spectator, the inner surfaces of the single conduits 37 which lead to the individual viewing chairs (as well as all other conduits) are kept extremely small. In FIG. 8, a correspondingly miniaturized single conduit 37 is depicted in the preferred original size.

At the same time, the air is enriched rather thoroughly with perfumes or scents in the scent carrier 10 or the scent helix 29 so that the desired scent can already be perceived when very small amounts of air are supplied.

As compared to certain air-conditioning apparatus in large halls where the conditioned air sometimes is conveyed to individual seats in large pipes, the inner surfaces of the single conduits 37 used according to the invention are extremely miniaturized, e.g. to $\frac{1}{1000}$ of the inner surfaces of single conduits of such apparatus, i.e. to surfaces of about 8–12 mm$^2$, or inner diameters of 3–4 mm.

Accordingly the amounts of air, which are distributed by such a micro air system, are very small Preferably, less than 1 liter of air is discharged per second, preferably only about 0.3 to 0.005 l/sec.

Depending on the extent to which perfumes or scents can be added to the quantities of air used, the inner surfaces of the conduits of other embodiments (not shown) can be reduced to less than $\frac{1}{10,000}$ of conventional air distribution systems. When the inner surfaces of the conduits are smaller than 2.5 mm$^2$, for example, only air quantities ranging from about 0.00001 to 0.005 l/sec. are emitted.

If scents are to be distributed by standard air distribution systems, e.g. air-conditioning apparatus, as was repeatedly tried without success before, about 1,000 to 10,000 times the amount of air has to be conveyed to every single spectator.

The great problems arising from the use of such a type of distribution system as a basis of scent systems for entertainment media, e.g. the general difficulty of precisely controlling the required amounts of air with technical means, the superposition of various scents in the showroom, the extraordinary cost of conventional, i.e. extremely large, distribution and air suction systems as compared to the system of the present invention, can be perfectly avoided by using a micro system.

The first-mentioned problem regarding the quick transfer and the very precise distribution of scents to the individual spectator can thus be solved by minimizing the transferred quantities of air and by simultaneously intensifying the introduction of scents. What has not yet been completely met is the requirement of discharging the scents at exactly the right time in coordination with the respective scenes of the movie.

Ad 2.) Synchronization of scenes:

The "fading in" of individual scents, which shall advantageously be synchronized with, or correspond to, the respective scenes in the movie can be achieved in various ways:

A.) The scent pulse is not emitted on the running film simultaneously with the associated movie scene but a few seconds earlier, i.e. so much in advance as it takes a scent to be transformed from a pulse on the film and to reach the spectator. Hence, if it takes 5 seconds for a scent signal emitted on the film to be transformed into a scent, and for the scent to be conveyed to and perceived by the spectator, the corresponding pulse 18–21 (FIG. 3) will be supplied from the running film stock 12 to the pulse scanner 4 in the projector 1 (FIG. 1) 5 seconds before the relevant scene.

In the present embodiment, the pulse scanner 4 first scans the somewhat further advanced "pre-code" pulse 18 and thus activates the scent roll controlling means 13 which thereby activates the scent carrier 10 on the scent roll 9 or 9a, whereupon said scent carrier is positioned in front of the scent connecting piece 25 (FIGS. 4 and 5).

On account of the other pulses 19–21, which have been advanced a little less, the degree of opening of the scent intensity controlling means 33 and the airflow controlling means 32 (FIGS. 6 and 5) is selected in order to bring about the introduction of the scene-related scent; the advance depends on the distance from the opened scent carrier 10 to the scent dispenser 28 at the viewing chair 16 (FIGS. 1 and 11) and the spectator.

However, as the distance from the projector 1 or the scent switch box 7 to the spectator (FIG. 1) is not the same in different movie theaters, the pulses on the film stock 12 should be advanced to such an extent that the advance suffices for a movie theater of maximum size.

In smaller movie theaters where the distances are shorter and quicker to cover, the signal advance is electronically delayed in the pulse scanner 4 or the scent roll controlling means 13 so that the scene-related scent will not be perceived too early. Hence, if a signal adapted to a maximum-sized movie house appears on the film stock 12 with a 6-second advance, in a smaller movie theater where only an advance of 4 seconds is required, said signal will be passed on to the scent roll controlling means by the pulse scanner 4 with a delay of two seconds.

Alternatively, to achieve the same effect, the rate of flow through the shorter conduits of smaller cinemas can be correspondingly adjusted by changing the conduit diameters, by slowing down the pumping rates of the compressor 6, or by other slowing-down mechanisms.

Another problem may arise when the film 12 tears and the portion comprising the pre-code 18 for selecting the scent carrier 10 is missing (FIG. 3). In this case, the subsequent scent pulses 19–21 would relate to a wrong pre-code 18. For this reason, each pre-code 18 is signalled twice, first at the actual advance time, then directly before the associated pulse.

Thus the scene-related scent is conveyed with a short delay when a portion of the film is missing because the film has torn but it is still associated with the correct scene.

However, since the missing film portion might also comprise scent pulses 19–21 and the order might thus be confused on the whole, all pulses on the film are additionally provided with a numerical identification 22 (FIG. 3) which can be read by the pulse scanner 4 (FIG. 1).

The continuously numbered identifications 22 have characteristic numbers which correspond to the numbers of scent carriers 10 associated with the respective scenes and encoded accordingly on the scent roll 9 or 9a (FIGS. 4 and 5).

Encoding of the scent carriers may be relinquished if the respective scent carrier 10 is localized by the scent roll controlling means 13 merely on the basis of its position within the scent roll 9. A "0-position" 46 on the scent roll 9 associated with the beginning of the film serves as reference point for the scent roll controlling means 13 for that purpose (FIG. 4).

Before any scent signal is passed on, the pulse scanner 4 or the scent roll controlling means 13 first checks whether the correct scent carrier 10 has been selected on scent roll 9 or 9a; if the identifications do not coincide, an appropriate number of scent carriers 10 are skipped and the correct scent carrier 10 is selected (FIGS. 4 and 5).

This means that, if pulses are missing, one scene is performed without the intended scent, but for the next scene the "wrong" scent of the previous scene is skipped on account of the numerical identification and the correct scene-related scent is introduced.

As regards the further transfer of the enriched air to the spectator, several modes of operation of the compressed-air conduit 8 divided into the main conduits 35, distribution conduits 36 and single conduits 37 can be employed.

In the present embodiment, the electric compressor 6 only generates a very small excess pressure which is just high enough to continue to the air outlet at the scent dispensers in the armrests 27 of the individual chairs 16.

In this process, a constant flow of air between the electric compressor and the chair 16 is maintained; as described above, however, the airflow is very small due to the very small single conduits 37 and almost goes unnoticed by the spectators except when scent is dispensed.

B.) In another embodiment (not shown), the individual scent control pulses are also emitted by the running film stock some time before the associated scene, whereupon the perfumes or scents are also conveyed in the compressed-air conduit 8 and towards the spectators.

In this case, however, the airflow is stopped at the last distribution unit, the final distributor 17, by a distribution valve 41 (not shown) as soon as the enriched air arrives there. A certain excess pressure, here: 0.6 atmospheres over atmospheric pressure, for example, is thus built up in the whole conduit.

The correct closing time of the distribution valve 41 at the final distributor 17 is input over a predetermined time interval, for instance, which corresponds to the time of flow of the scent stream from the scent carrier 10 to the final distributor 17 and which is determined when the conduits are assembled (see FIG. 1).

For example, if it takes 3 seconds for the scent from getting from the scent carrier 10 to the distribution valves 41, the pulse scanner 4 (or, alternatively, the scent roll controlling means 13) transmits a closing signal to the distribution valves 41 via a signal line extending directly to the distribution valves 41 3 seconds after a scent has been input.

Alternatively, the correct closing time of the distribution valves 41 can also be determined by means of an air quantity-controlled closure which closes when the quantity of air required for the distance from the scent carrier 10 to the distribution valve 41 has flown through.

In this embodiment, the scene-related scent is thus conveyed almost up to the viewing chair 16 to the final distributor 17 a long time before the associated scene is shown, and is "stored" there for a while. The valves in the final distributors 17 open just before the associated scene is shown in response to a specific valve pulse 23 applied on the film stock (FIG. 3), said valve pulse being transmitted from the pulse scanner 4 via the lines extending directly to the distribution valves 41 at the final distributors 17. Immediately thereafter, the enriched air is conveyed over the final, short distance to the spectator.

Contrary to the previous embodiment, there is no discharge of air at the viewing chair in the present embodiment unless scent is to be supplied to the spectator.

Such a technique requires that the valves be designed in a manner that they operate with so little noise that they do not disturb the audience during the motion picture show.

C.) in another embodiment (not shown), which is a very useful combination of the two afore-mentioned examples, the scent pulses 18–21 are also emitted some time before the respective scenes.

In this case, the compressor 6 also conveys the enriched air almost to the individual chairs 16, however, without building up an excess pressure in the conduit. Subsequently, the further air supply from the compressed-air conduit 8 is diverted or blocked by a compressor valve 63 at the compressed-air conduit 8 (FIGS. 5 and 7). By turning off the further air supply in the compressed-air conduit 8, the enriched air also stops in all further branches of the conduit and thus also in the single conduits 37 a few meters before the outlet at the chairs.

The scent can be reliably prevented from independently and prematurely spreading to the chairs 16 by the extremely small diameter of the single conduits 37 (shown in original size in FIG. 8) and by the very short time which it is retained in the conduit. The correct closing time of the compressor valve 63 (FIG. 5 or 7) is achieved via a programmed time interval or a flow rate switch, as in the previous embodiment.

The air pressure generated by the compressor 6 is re-introduced in the compressed-air conduit 8 only immediately before the respective scene in response to a corresponding signal, e.g. the valve signal 23, which in this case leads to the compressor valve 63, however, so that the airflow continues towards the armrests 27 of the chairs 16 and the corresponding scent is discharged (FIG. 1).

D.) In another embodiment shown in FIG. 2, the length of the distance between scent carrier 10 or scent switch box 7 and the individual viewing chairs 16 is considerably reduced in that the scent switch box 7 is not mounted in the projectionist's cabin as in FIG. 1 but in the middle of t he movie theater in the place of the previous main distributor 11 which is now the central scent switch box 11a (FIG. 2).

Figure 2:
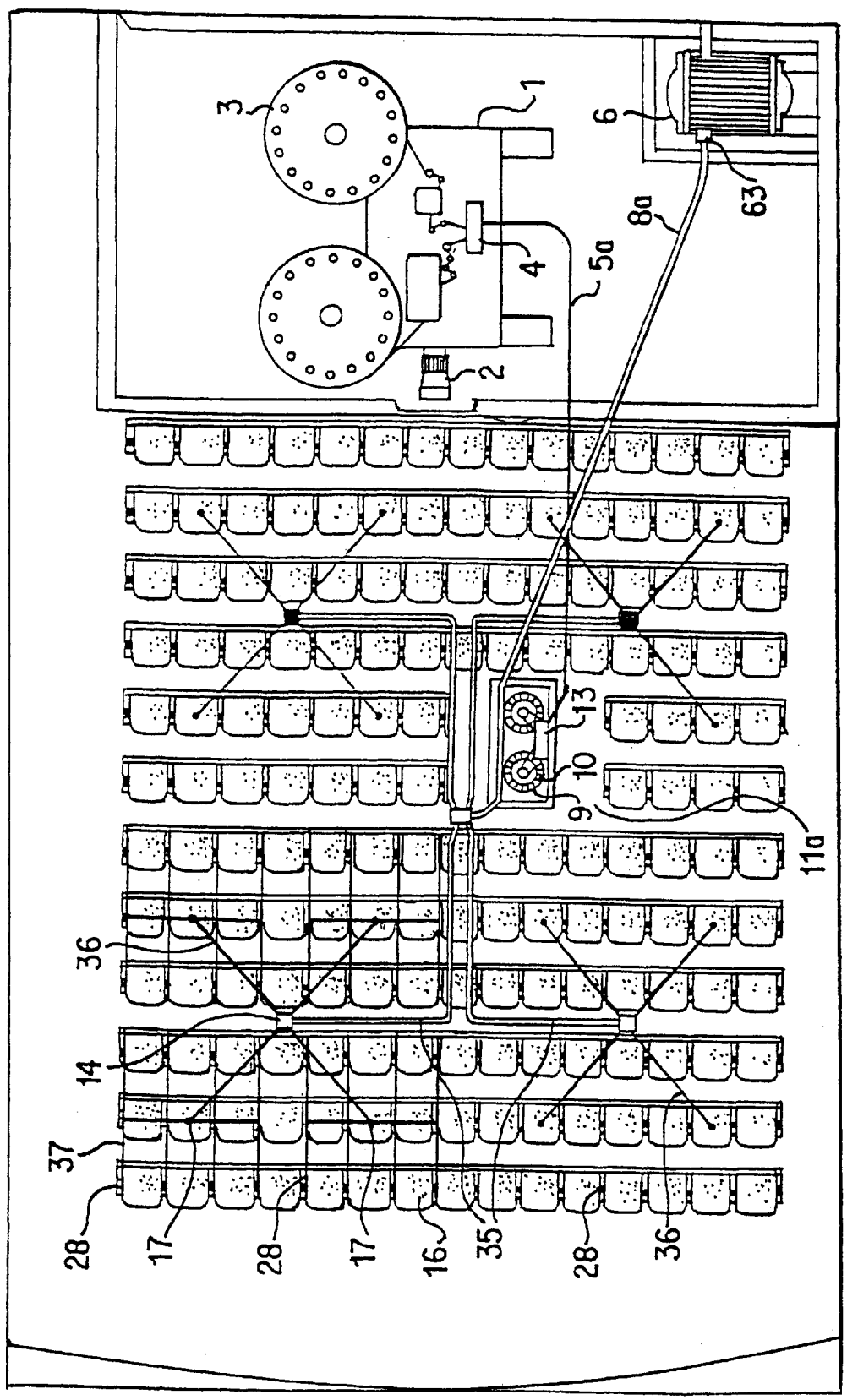
FIG. 2 is a schematic view of another embodiment of the aroma cinema.

Accordingly, the compressed-air conduit 8a and the signal line 5a extend directly to the central scent switch box 11a, i.e. the center of the showroom (FIG. 2). In this way, the distance to the chairs 16 can already be reduced to such an extent that the signal advance of the scent pulses 18–21 may perhaps be relinquished, so that the pulses 18–21 only have to be emitted from the running film stock directly before the associated scene.

E.) In another reduction step (not shown), the scent switch box 7 is placed even closer to the viewing chairs 16, namely in the place of the previous intermediate distributor 14, so that the four simultaneously operating scent switch boxes 14a are obtained; the corresponding compressed-air conduits and signal lines are also extended to said four scent switch boxes 14a.

Of course, a precondition for the displacement of the scent switch boxes 11a/14a into the auditorium in the last two embodiments is that the introduction of air into the scent carrier 10 can be carried out with so little noise in the auditorium that the spectators are not disturbed.

F.) In another embodiment (not shown), a distribution system (components 8, 35, 36, 37, as in FIG. 1 or 2) also extends to all of the viewing chairs 16 but in contrast to the afore-mentioned embodiments, no scent is introduced into the distribution system until the viewing chair 16 has been reached. Only then, at the chair 16, a scent program is supplied from a very small feeding system which is connected to the distribution network or a single line 37.

The scent programs can be stored in many possible ways, e.g. in the "scent discs" (FIG. 17) described further below, etc.

As regards the afore-mentioned possibilities concerning the fading-in, fading-out or crossfading of scents, however, the last-mentioned system is not nearly as adjustable and multifarious as the afore-mentioned systems, if it is to be provided at a reasonable cost. For this reason, the objective of a perfect illusion cinema as an overall piece of art can only be achieved to a limited extent.

The afore-described possibilities can also be combined for forming further processes.

Ad 3.) Simultaneous perceptibility

In order to solve the third part of the object, namely to enable the enriched air to be emitted at all viewing chairs 16 at the same time, the conduits leading to all the chairs are constructed such that they all have the same length (this embodiment is not shown). If the distances from some conduits to certain chairs are shorter than others, the missing distance is compensated for by way of empty or compensating windings at the short conduits in such a manner that the air is discharged therefrom exactly at the same time and with the same intensity.

In another embodiment (not shown), the diameters of the individual conduits are adjusted to one another such that the air is simultaneously discharged at the scent armrests 27 of all chairs 16 and thus is made perceptible at the same time.

In another embodiment (not shown), simultaneous perceptibility is achieved by specific valve operation in the conduit system. As already described in connection with the synchronization processes B and C, the enriched air is first also conveyed to the final distributors 17 before the associated scene. There the scent is also stored, as a distributor valve 41 which is controlled on the basis of air quantity or time interval stops the enriched air as soon as it reaches the valve.

Shortly before the associated scene appears on the screen, a valve pulse 23 (FIG. 3) is also supplied to the distributor valves 41.

The valves do not open at the same time, however.

In the present case, the opening times of the distributor valves 41 from whose conduits 37 the scents are emitted somewhat too early are slightly delayed during the installation of the scent conduit system so that the enriched air finally leaves from all single conduits 37 at the same time.

Further alternatives of ensuring simultaneous perceptibility of scents during the showing of a motion picture can be obtained by combining in various ways the individual processes described above.

Hence, the three requirements

1.) "speed and minimization" of the transmission of scent;

2.) "synchronization of scenes", i.e. the release of scent in accordance with associated scenes;

3.) "simultaneous perceptibility" of scent are substantially met for all spectators.

In order to ensure perfect enjoyment of scents for every single spectator, however, it is probably recommendable that the perceptible scents be adjustable individually. This can be done at little expense.

As compared to pictures, sound and music, the perception of perfumes and scents differs more strongly from individual to individual. For this reason, it might be important that a spectator is enabled to adjust the intensity of released scents individually and, if necessary, turn the scents off completely.

So as to enable the spectator to adjust the intensity of scents individually, a scent dimmer 70 (FIG. 11) is provided e.g. at the right armrest 27 of each viewing chair 16 so that spectators with a sensitive nose may render the scents weaker or turn them off completely.

The scent dimmer 70 is connected directly to a viewing chair scent controlling means 72 which is also disposed on the armrest 27 but which is not visible to the spectator (shown approximately in original size in FIGS. 9 and 10).

If the scent dimmer 70 is turned down, a corresponding portion of the scent supplied is diverted directly into a return conduit 56 via a small conduit controlling means 61 before reaching the outlet at the chair (FIG. 9 or 10, where the scent dimmer is closed completely).

For this purpose, not a single conduit 37 but a twin conduit 45 is laid to every seat, which is shown approximately in its original size in FIG. 8 to demonstrate the proportions.

As far as the costs for the installation of such conduits are concerned, it does probably not matter whether a single conduit 37 or a twin conduit 45 is used.

As the conduit material (which preferably consists of very cheap, odor-resistant plastic conduits) is not very expensive anyway, the costs of a twin conduit 45 hardly differ from those of the extremely inexpensive single conduit 37. This means that it is possible to accompany movie scenes with scents in an individually adjustable manner at a negligible additional expense. Moreover, the return conduit 56 of the twin conduit 45 can also be used for a second function at the same time.

If the scent supply conduits 37 leading to the chairs are used for several performances every day, parts of the conduit system might take on certain smells, e.g. scents which are often used, in course of time. Even if the conduits are designed such that they do not take on smells, it is possible that residues or condensation water are formed in the conduits, which might also produce unwanted odors.

With the aid of the return conduit 56 already laid to the seats, the scent conduit 37 can easily be cleaned once a month, for instance, by setting the scent dimmer 70 disposed on the chair at "zero", whereupon the viewing chair scent controlling means 72 is completely closed (FIG. 10).

Instead of air, a cleansing liquid is now passed through the conduit 37, followed by warm drying air, which then flows back to the pumping means via the return conduit 56, thus removing any impurities.

Instead of a pumping means, this operation can also be carried out by the electric compressor 6 already installed, if the compressed-air conduit 8 extends into a supply device after the compressor, said supply device providing the cleansing liquid and subsequently taking it back from the return conduit 56.

In this manner, any impurities in the conduits which might be caused by constant long-term operation can easily be removed.

In this process, the minute, inexpensive twin conduit 45 (FIG. 8) consisting of the single conduit 37 and the return conduit 56 can thus carry out the three most essential operations of the scent conduit system:

a) supplying the scene-conforming scents, b) diverting scents considered too strong by individual spectators, and c) cleaning the conduit system, if necessary.

This means that movie theaters can be converted at very little expense on the basis of the above-described systems so that the new and fascinating technique of accompanying movie scenes with scents can be applied.

As the individual scents arrive precisely and synchronous with the associated scenes and are adjusted to the individual spectator's wishes as described above, it may also be necessary to prevent the scents from lingering in the auditorium for too long in order to avoid the superposition of several scents. For this purpose, the scene-related scents can be released from the armrests 27 of the chair 16, i.e. from the scent dispenser 28 (FIG. 11), at a temperature which is about 3 to 5 degrees higher than the temperature in the auditorium, for example, so that the scent-enriched air rises upwards. The upward movement can be supported by a suction apparatus of a common air conditioner in the ceiling of the movie theater.

A technically even more effective way of having the scents linger in the auditorium for only a short time is to add to the scene-related scents certain blends of highly volatile elements, e.g. helium, argon or xenon. The very small amount of air discharged thus has a considerably lower specific gravity than the ambient air, which results in the rapid removal of the emitted scents. The upward displacement of air can also be brought about or supported by imparting a rotaty motion (whirlwind principle) on the small quantity of air discharged by guiding the air in a suitable helical form.

The suggested blends e.g. of helium and breath, do not bear any health risks, as corresponding mixtures have successfully been used for decades in scuba diving, where they facilitate the breathing of divers under water.

Another way of preventing the scents from lingering about the viewing chairs for too long is to install so-called scent resorbers 15 preferably in the upper edge of the backrests of the chairs or in other appropriate places on the chairs (FIG. 11). The scent resorbers 15 evacuate the superfluous scents so that they are no longer perceptible.

In this embodiment, a constant but very weak airflow can be generated between the scent dispensers 28 and the scent resorber 15, as is shown in FIG. 11 near one of the viewing chairs. The amount of air moved is so small, however, that it will not irritate the eyes, nose, etc.

However, the airflow might have the effect of enabling the spectator to perceive the individual scene-related scents substantially regardless of whether his/her head is bent forward or backward at that moment, i.e. the scent can be perceived uniformly and with the same intensity irrespective of the spectator's posture in the seat.

Figure 13:
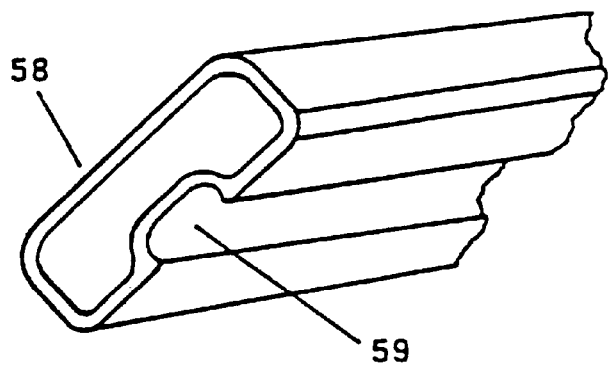
FIG. 13 is a top plan view of a scent resorbing conduit (58) of another embodiment.
Figure 14:
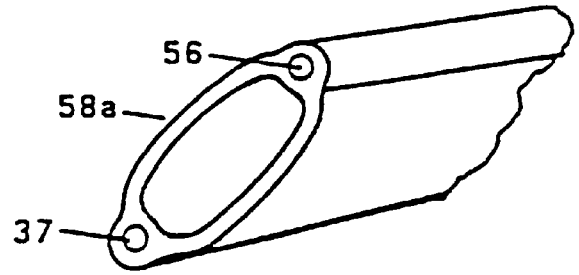
FIG. 14 is a top plan view of a scent resorbing conduit (58*a*) of another embodiment comprising an integrated single conduit (37)

The scent resorber 15 is connected to a resorber conduit 58 which is preferably much larger than the single conduits 37 (FIGS. 13, 14 and 8).

If a resorber conduit 58 is installed, the conduits are designed such that, in order to facilitate the laying thereof, the single conduit 37 and the return conduit 56 form an integrated whole with the resorber conduit 58 (FIG. 14) or are firmly connected thereto in the form of twin conduit 45 (FIG. 8) via a retaining groove 59 (FIG. 13).

When the new and fascinating medium of scent-accompanied motion pictures has been widely accepted in the world of entertainment, there may arise the desire to employ these techniques also outside movie theaters. For this reason, decentralized modes of application might be of interest some day; the following two applications are particularly tailored thereto (FIGS. 15–17).

One embodiment of the invention, the so-called scent composer 50, depicted in FIG. 15, is particularly suited for use in small rooms, for decentralized applications and for scent presentations which shall involve fewer expenses and technical efforts. The scent composer 50 can thus also be used to accompany music performances, slide shows or video shows and TV programs.

The operating principle of the scent composer 50 differs substantially from that of the foregoing embodiments.

In the present case, the scents to be used are not yet completed, as in scent rolls 9 and 9a of the embodiments illustrated in FIGS. 4, 5 and 7; rather, all of the perfumes or scents required are produced shortly before being used by connecting in succession a number of scent mixing rolls 51 (FIG. 15).

In the scent composer 50, e.g. five scent mixing rolls 51, each containing 12 basic scent components, for example, are connected in succession. Frequently used basic components may also be present several times in individual scent mixing rolls. In this manner, about 250,000 different scents, or 25,000 different scents in 10 different degrees of intensity, can be produced on the basis of 60 basic components.

By means of a small crossflow blower 54 inside the scent composer 50 which runs at somewhat lower speeds than other blowers of said low-noise type and therefore produces extremely little noise, air is passed via the supply conduit 49 through the basic scent components present within the supply conduit system. The air flowing via supply conduit 49 through the individual components of the five scent mixing rolls 51 assumes the specific scent of each of said components while passing therethrough, so that a specific aroma combining these scents has been produced at the end of the conduit.

In order to avoid a possible aroma transfer as described before in connection with FIG. 7, the weakest of the basic scent components are disposed in scent mixing roll 51 where the air from the crossflow blower is introduced first; the strongest scent components are contained in scent mixing roll 51 where the air passes through last, i.e. shortly before leaving the scent composer 50.

So as to prevent the scent components disposed outside the supply conduit 49 from giving off their scent prematurely, they are provided with partition walls 47 (in FIG. 15, the first partition wall is not shown).

Another possible way (not shown) of protecting the individual basic scent components from premature scent loss without complex valve systems is to arrange the scent components in the scent mixing rolls 51 in such a manner that they do not emit scent at normal room temperature in the range from 18 to a maximum of 35 degrees. Only when the air from the crossflow blower passes through a small heating spiral before entering the scent mixing rolls 51 and is heated to a somewhat higher temperature, e.g. 50 degrees, do the scent mixing rolls 51 emit their scents through the heated air.

After leaving the scent mixing rolls, the heated blend of scents can be cooled down to room temperature in a small cooling spiral or, depending on the type and length of conduits, cools down on its own on the way to the spectator.

The scent to be produced is supplied to the mixing roll controlling means 52 via a five-digit control pulse through a signal cable 60.

Hence, this kind of scent production and control also permits a decentralized application of the scent composer 50.

For example, the signal line leading to the mixing roll controlling means 52 can be connected to a video recorder or a TV terminal, the scene-related control pulse being transmitted to the TV via a radio signal.

A scent composer of this kind is thus adapted to produce the appropriate scents in various places for the most varying movies, as it is required for TV programs, for instance.

As the scent composer is adapted to produce different degrees of intensity of each scent, gradual supplies of scents can be realized, too.

When the scent mixing rolls 51 are exhausted, they can be replaced individually or as a complete set.

As compared to the extremely precise and variable scent processes employed in movie theaters as described above, however, the scent composer 50 has its limitations with respect to perfection of application and is restricted to applications of low standards.

A further embodiment which is easier to realize can be seen from FIGS. 16 and 17.

This embodiment is also intended for decentralized use. However, the required scents are not mixed as in the case of the scent composer 50 but are stored on a small scent disc 57. Similar to a miniaturized scent roll 9 of the first embodiment (FIG. 4), the scent disc 57 contains the scents required for a specific movie. In the scent disc, the scents are stored in small scent carriers (not shown) which may have different shapes suited for the purpose.

Similarly, in principle, to the disc drive of a conventional computer, the scent disc drive 55 shown only schematically (FIG. 16) is adapted to select the appropriate scent of the disc 57 via the drive connector 71 and a drive recess 76 of the disc 57 (FIG. 17). The information where each scent is stored is conveyed to the scent disc drive 55 by the position of the drive recess 76, for instance.

Similar to the scent composer 50 (FIG. 16, component 54), a low-speed and therefore extremely low-noise crossflow blower 78 is arranged in the casing of the scent disc drive 55 (FIG. 17). From this crossflow blower 78, an airflow is blown into the disc scent duct 79 via a corresponding air conduit 80 (similar to the component 49 in the scent composer of FIG. 15). Subsequently, the scents from the scent carrier which is positioned in front of the scent duct 79 of the film scent disc 57 at that time is passed into the air conduit 80 and finally led out of the casing to the TV viewer (FIG. 16).

As there is only relatively little space on such a small disc, only the most important scents required in the movie are stored therein. The maximum volumetric capacity of such a scent disc is about 30 scents in a disc of e.g. 9×9×1.5 cm.

The volumetric capacity of these miniaturized scent carriers is very limited so that a scent disc 57 can be used only 1 to three times, depending on its design.

After the scent disc 57 has been inserted in the scent disc drive 55, the scent disc drive 55 first automatically selects a socalled "zero position" (not shown) in the scent disc 57. The zero position is located before the position of the first scent to be introduced in a movie and simply is an empty cycle in the disc where no scent is emitted. When a scent introduced during the film is terminated in accordance with the respective scene, the disc returns to said zero position.

In this manner, the end of each scent release can be selected by the disc drive 55 without the need for additional valves, etc. or without having to turn the blower 78 on and off each time.

The scent disc drive 55 is connected to a video recorder, a TV terminal, a radio or a slide projector, for example, via a signal cable 60.

When a motion picture, music program, musical, theater or ballet performance, etc. is shown, the control commands required for controlling the film scent disc 57 are transmitted in the form of inaudible control signals along with the respective program.

The signals can be read by an additional device connectible to the TV apparatus and are then conveyed to the scent disc drive 55 via the small signal cable 60. Said additional device or reading means for the scent signals can also be located within the scent disc drive 55 so that the drive 55 can be directly linked to a connector of the TV receiver via the signal cable 60. In response to the scent signals transmitted, the scents associated with the respective scenes are introduced into the scent conduit 80 and passed to the spectator e.g. via a tiny, short conduit.

In order to effect long-term protection of the tiny amounts of air storable on a scent disc 57 against premature volatilization, the scent disc 57 is sealed in a foil before being sold, which foil is only removed when the TV viewer uses the disc for the first time.

If the system is widely used, it will be possible to sell the scent discs 57 of certain particularly popular movies to be shown on TV via retailers, such as magazine stores, etc.

Beside being used to supplement video shows and TV broadcasts with scents, the film scent disc 57 can also be employed in small public show rooms for music, theater or motion picture performances which cannot profitably be equipped with a specific scent system as the ones for movie theaters as described above.

The scent disc system can also be used for open-air concerts or other open-air shows to be accompanied by scents (e.g. open-air cinema). In this case, each seat is provided with a small disc drive 55 into which the appropriate scent disc 57 in inserted to accompany a slide show, music performance, open-air movie show, etc.

If it is too expensive or complicated to lay signal cables 60 to all scent disc drives 55 in major shows, it is also possible to activate the disc drives via a radio signal.

List of Reference Numbers (1) film projector
(2) projection lens
(3) film roll
(4) pulse scanner piece
(5) signal line
(5a) signal line
(6) electric compressor
(7) scent switch box
(8) compressed-air conduit
(8a) compressed-air conduit
(9) scent roll
(9a) second scent roll means
(10) scent carrier controlling means
(11) main distributor
(11a) central scent switch box
(12) film stock
(13) scent roll controlling means
(14) intermediate distributor
(14a) scent switch box
(15) scent resorber
(16) viewing chair
(17) final distributor
(18) pre-code
(19) full pulse
(20) partial pulse
(21) negative partial pulse
(22) numerical identification

(23) valve pulse
(24) sealing material
(24a) sealing zone
(25) scent connecting
(26) scent lamella
(27) scent armrest
(28) scent dispenser
(29) scent helix
(29a) half of scent helix
(30) electronic bar code
(31) pipe collar
(32) air flow controlling
(33) scent intensity
(34) pilot signal
(35) main conduit
(36) distribution conduit
(37) single conduit
(38) control system
(39) control terminal
(40) inlet opening
(41) distributing valve
(42) outlet opening
(43) sealing flap "on"
(44) sealing flap "off"
(45) twin conduit
(46) 0-position at the beginning of the film
(47) partition walls
(48) screen
(49) air supply conduit
(50) scent composer
(51) scent mixing rool
(52) mixing roll controlling means piece
(53) disc receiver controlling
(54) crossflow blower means
(55) scent disc drive
(56) return conduit means
(57) scent disc
(58) resorber conduit
(58a) resorber conduit
(59) retaining groove
(60) signal cable
(61) conduit control
(62) contact mechanism
(63) compressor valve
(64) scent grid
(65) -
(66) scent opening
(67) running surface
(68) air supply conduit
(69) control wheel
(70) scent dimmer
(71) drive connecting
(72) viewing chair scent means
(73) journal bearing
(74) journal securing
(75) -
(76) drive recess
(77) computer connector
(78) crossflow blower
(79) disc scent conduit
(80) air conduit

I claim:

1. Process for intensifying sensorial perception of visual and/or acoustic presentations, including supplying an audience with suitable scents in synchronism with the presentation of specific visual and/or acoustic events or scenes, wherein the scents are supplied in the form of a scent-enriched scent/air mixture stream enriched with an ingredient of sufficiently low specific gravity so that the emerging scent/air mixture is lighter than the ambient air.

2. Process according to claim 1, wherein the ingredient is helium.

3. Process according to claim 1, wherein the supplying step comprises supplying the scent through miniaturized conduits at a rate less than one liter of air per second to an individual spectator.

4. The process according to claim 1, wherein the supplying step comprises supplying the scent at a rate of from 0.3 to 0.005 liters per second.

5. The process according to claim 1, wherein the supplying step comprises supplying the scent at a rate of from 0.3 to 0.0001 liters per second.

6. Process according to claim 1, wherein the respective scents are individually supplied from a scent reservoir in response to at least one selection signal.

7. Process according to claim 1, including adjusting the intensity of supplied scents to correspond to the individual presentations.

8. Process according to claim 1 including increasing the intensity of supplied scents with time.

9. Process according to claim 1 including decreasing the intensity of supplied scents with time.

10. Process according to claim 1, wherein the respective scents are supplied to, and/or evacuated from, the audience separately or in groups.

11. Process according to claim 1, including evaluating the supplied scents during and/or after the associated events of the presentation.

12. Process according to claim 1, wherein the scent-enriched scent/air mixture stream is discharged at a temperature which is 3 to 5 degrees higher than the temperature of the ambient air.

13. Process according to claim 1, wherein a rotary whirling motion progressing in the direction of flow is imparted on the emerging scent/air mixture so that said scent/air mixture flow forms a directional flow channel over a predetermined distance after being discharged.

14. A device for intensifying sensorial perception of visual and/or acoustic presentations, comprising a scent supplying mechanism including miniaturized conduits for supplying an audience with suitable scents being supplied in the form of a scent-enriched scent/air mixture stream enriched with an ingredient of sufficiently low specific gravity so that the emerging scent/air mixture in lighter than the ambient air.

15. The device according to claim 14, wherein the ingredient is helium.

16. The device according to claim 14, wherein the supplying step comprises supplying the scent through miniaturized conduits at a rate less than one liter of air per second to an individual spectator.

17. The device according to claim 14, wherein the supplying step comprises supplying the scent at a rate of from 0.3 to 0.005 liters per second.

18. The device according to claim 14, wherein the supplying step comprises supplying the scent at a rate of from 0.3 to 0.0001 liters per second.

19. The device according to claim 14, wherein the inner diameter of each of the single conduits is from 3 to 4 mm.

20. The device according to claim 14 including an arrangement for individually storing and releasing various scents, and an associated arrangement for controlling the release and supply of specific scents in accordance with respective visual and/or acoustic events.

21. The device according to claim 14 including an arrangement for individually storing and releasing various scents, and an associated arrangement for controlling the release and supply of specific scents in accordance with respective visual and/or acoustic events.

22. The device according to claim 20, wherein the scent storing and releasing arrangement comprises a plurality of different scent reservoirs selectively made available by a scent supply selecting means.

23. The device according to claim 20 including a source of scents in releasable solid form.

24. The device according to claim 20 including a source of scents in releasable liquid form.

25. The device according to claim 20 including a source of scents in the form of pressurized gas.

26. The device according to claim 14 including scent reservoirs in the form of at least one scent switch box.

27. The device according to claim 14 including scent reservoirs in the form of at least one scent disc.

28. The device according to claim 14 including scent reservoirs in the form of at least one scent roll arrangement.

29. The device according to claim 14 including a scent storing and releasing arrangement including a scent intensity controlling mechanism.

30. The device according to claim 29, wherein the scent storing and releasing arrangement comprises a spiral-shaped conduit system including inlet and outlet control elements and an associate by-pass conduit for introducing the respective scent into an air flow.

31. The device according to claim 29, wherein the scent storing and releasing arrangement comprises at least two contact surfaces for air flow parts for introducing the respective scent into an air flow.

32. The device according to claim 29, wherein the scent storing and releasing arrangement comprises a scent mixer for several basic scent components provided in scent mixing rolls activatable by single air flow.

33. The device according to claim 29, wherein the scent storing and releasing arrangement comprises a mobile unit connected with scent discs.

34. The device according to claim 29, wherein the scent storing and releasing arrangement comprises a mobile unit connected with a scent mixer.

35. The device according to claim 29 including scent mixing rolls for contacting the scents sequentially, and a blower for generating air flow.

36. The device according to claim 29 including scent reservoirs having sealing means protecting against scent loss.

37. The device according to claim 29 including scent reservoirs having a temperature responsive scent release mechanism.

38. The device according to claim 29 including a scent release mechanism having a detector for supplying a scent control signal synchronous with respective events of the presentation.

39. The device according to claim 38, wherein the detector receives optical and/or electric scent control signals containing encoded data on the type of scent and/or composition of scent and/or age of scent reservoirs and/or frequency of use of the scent reservoirs and/or the duration of scent supply.

40. The device according to claim 38, wherein the scent control signals contain data relating to scent intensity, the beginning and end of scent supply, and the change of scents.

41. The device according to claim 38, wherein encoded film tracks or event-coupled signal transmitters are provided as scent control signals.

42. The device according to claim 38 including an arrangement for activating the release mechanism comprising a source of compressed air.

43. The device according to claim 42 including a scent distribution system comprising controllable scent outlets for groups of chairs and/or individual chairs of the audience.

44. The device according to claim 43 including a scent evacuation system for individual chairs and/or groups of chairs connected to the scent distribution system.

45. The device according to claim 43, wherein the scent distribution system comprises conduits having adjustable lengths and diameters.

46. The device according to claim 45, wherein the conduits comprise two conduits with supply and return conduits for adjusting scent intensity individually at each chair.

47. The device according to claim 46, wherein pairs of helical ducts are arranged to perform rotary motions in opposite directions to generate a tangential directional scent/air mixture stream.

48. The device according to claim 41 including pivotably mounted scent outlets for adjusting the direction of discharge of the scent/air mixture stream.

49. Process for intensifying sensorial perception of visual and/or acoustic presentations, including supplying an audience with suitable scent in synchronism with the presentation of specific visual and/or acoustic events or scenes, wherein the scents are supplied from a unit in an amount of less than one liter of air per second.

* * * * *